US00PP35367P3

(12) United States Plant Patent
Walsh et al.

(10) Patent No.: US PP35,367 P3
(45) Date of Patent: Sep. 5, 2023

(54) APPLE TREE NAMED 'MD-TAP2'

(50) Latin Name: *Malus domestica*
Varietal Denomination: MD-TAP2

(71) Applicant: University of Maryland, College Park, College Park, MD (US)

(72) Inventors: Christopher S. Walsh, University Park, MD (US); Julia M. Harshman, Ventura, CA (US); Kathleen W. Hunt, Seabrook, MD (US)

(73) Assignee: University of Maryland, College Park, College Park, MD (US)

( * ) Notice: Subject to any disclaimer, the term of this patent is extended or adjusted under 35 U.S.C. 154(b) by 0 days.

(21) Appl. No.: 17/663,325

(22) Filed: May 13, 2022

(65) Prior Publication Data

US 2022/0418177 P1 Dec. 29, 2022

Related U.S. Application Data

(60) Provisional application No. 63/201,849, filed on May 14, 2021.

(51) Int. Cl.
*A01H 5/08* (2018.01)
*A01H 6/74* (2018.01)

(52) U.S. Cl.
USPC ..... Plt./161
CPC ..... *A01H 6/7418* (2018.05)

(58) Field of Classification Search
USPC ..... Plt./161, 172, 156
CPC ..... A01H 5/0875
See application file for complete search history.

(56) References Cited

U.S. PATENT DOCUMENTS

PP3,637 P 10/1974 McKenzie
PP4,382 P 2/1979 Wijcik
PP9,392 P 12/1995 Crosby et al.

*Primary Examiner* — Kent L Bell
(74) *Attorney, Agent, or Firm* — McKee, Voorhees & Sease, PLC

(57) ABSTRACT

A new and distinctive variety of *Malus domestica* Borkh, apple tree named 'MD-TAP2' is distinguished by its attractive tree architecture, reduced need for hand pruning and training, observed tolerance to high temperatures during the growing season, fireblight (*Erwinia amylovora*) and fruit which is harvested two weeks earlier than its seed parent.

5 Drawing Sheets

Latin name: *Malus domestica.*
Varietal denomination: 'MD-TAP2' (formerly F333).

BACKGROUND

The invention refers to a new plant variety of apple tree (*Malus domestica*) named 'MD-TAP2'. The new variety is distinguished by its attractive tree architecture, reduced need for hand pruning and training, and fruit which is harvested earlier than its seed parent. 'MD-TAP2' originated as an open pollinated seedling of a 'Fuji' (unpatented) apple tree planted in isolated block of apple seedling trees in Keedysville, (Washington County) Md. Those seedlings had been produced in a previous open pollination of a 'Dwarf McIntosh' (U.S. Plant Pat. No. 4,382, known as 'McIntosh Wijcik'™) tree located in an isolated block of 'Gala' (U.S. Plant Pat. No. 3,637) apple trees, also in Keedysville, Md. The original 'MD-TAP2' seedling was produced in 2002, germinated, grown in a greenhouse in College Park, Md., and then transplanted in Keedysville, Washington County, Md. in 2003. This original tree was observed to produce large, good-quality fruit annually during subsequent seasons. In 2015 budwood was taken from this original 'MD-TAP2' tree and bench-grafted onto clonal, non-dwarfing rootstocks of 'M.111' (unpatented). Grafted trees were planted in Keedysville, Md. They were observed from 2016 until 2021. During that time, the leaves, flowers, fruit, shoots and trunk were found to be stable and essentially similar to those on the original seedling tree.

BRIEF SUMMARY

The 'MD-TAP2' variety exhibits an exceptional apple tree architecture. With its mesotonic growth habit, wide-angle branches, shoot di-morphy leading to a spur-type habit, the tree canopy is open. Most fruiting shoots (spurs) receive full sunlight. Shoots are not rigid and arch downward with a typical crop load. Buds from the original seedling tree were vegetatively propagated in Cecilton, Md. by grafting on 'M.111' rootstocks. These were precocious; they began to flower and fruit in their third growing season. Despite limited training and pruning and grafting onto a non-dwarfing root stock, trees were manageable after six growing seasons. 'MD-TAP2' trees produce fruit similar to its seed parent 'Fuji' but differs in tree size and appearance. 'MD-TAP2' trees are smaller than 'Fuji' due to short pliable shoots, shorter internodes, a spur-type habit, and fewer pruning requirements. The fruit size of 'MD-TAP2' is medium and similar to that of 'Fuji', but matures earlier than that variety. It is a mid-to-late-September apple when grown in Keedysville, Md. In addition to maturing two weeks earlier than 'Fuji', the tree exhibits greater field tolerance to fireblight disease than 'Fuji' and 'Gala' apple trees.

BRIEF DESCRIPTION OF THE DRAWINGS

This new apple variety, 'MD-TAP2', is illustrated by the accompanying photographic drawings of the plant growing at the research farm in Washington County, Md. These drawings show the tree using color photography. Colors shown are approximate as they can depend on horticultural practices, weather conditions, and management strategies. Consequently the color characteristics of this new variety should be determined from the observations described herein rather than these drawings.

DETAILED BOTANICAL DESCRIPTION

Figure 1:
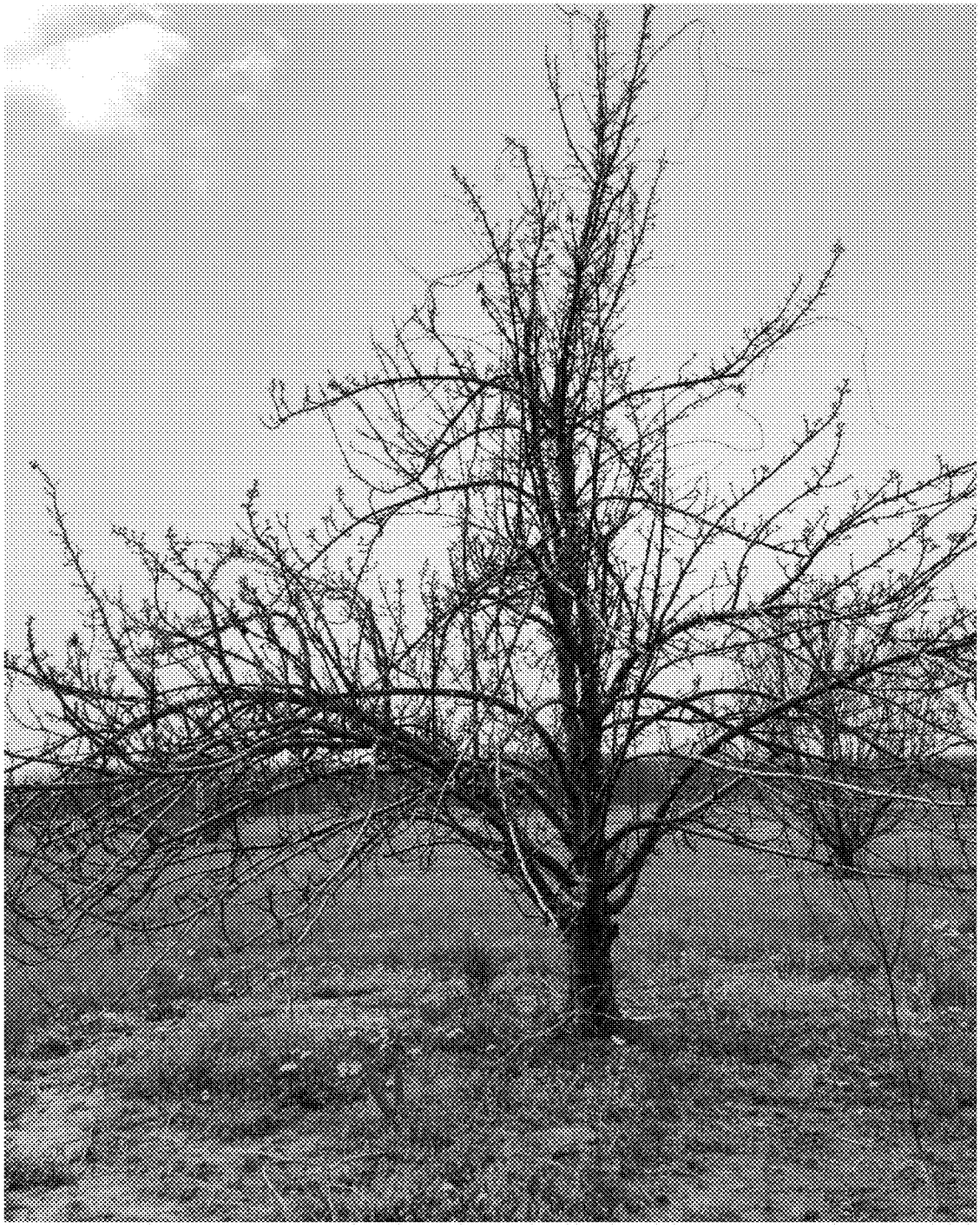
FIG. 1 is a color photograph taken on Apr. 13, 2022 of the original unpruned seedling apple tree 'MD-TAP2' during dormancy, showing its natural tree architecture.
Figure 2:
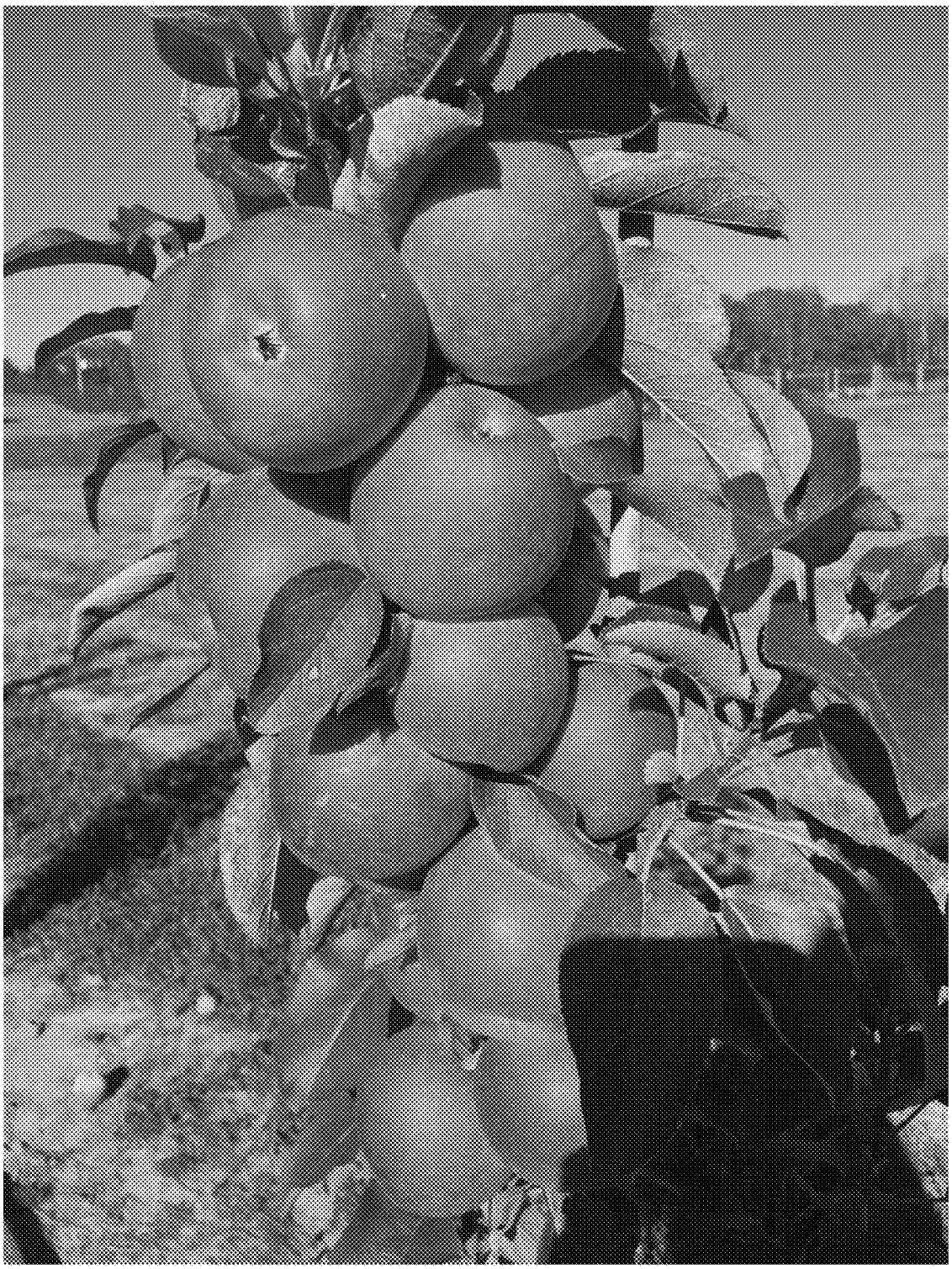
FIG. 2 is a color photograph taken on Oct. 2, 2017 of leaves and fruit on a single upright shoot of 'MD-TAP2' apple tree.
Figure 3:
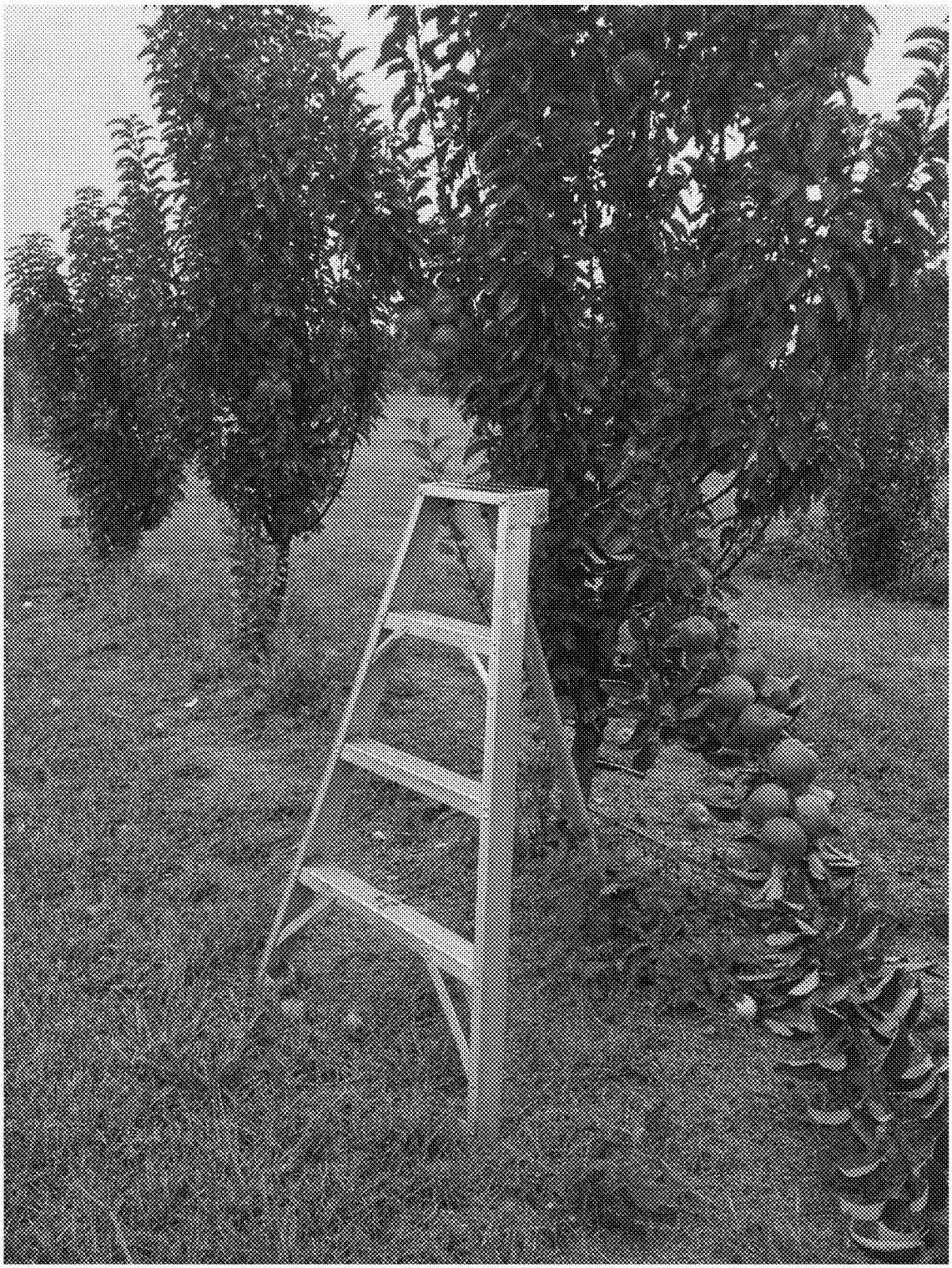
FIG. 3 is a color photograph taken on Sep. 30, 2019 of 'MD-TAP2' apple tree with a step ladder showing an upright branch being bent down with the weight of ripening fruit.
Figure 4:
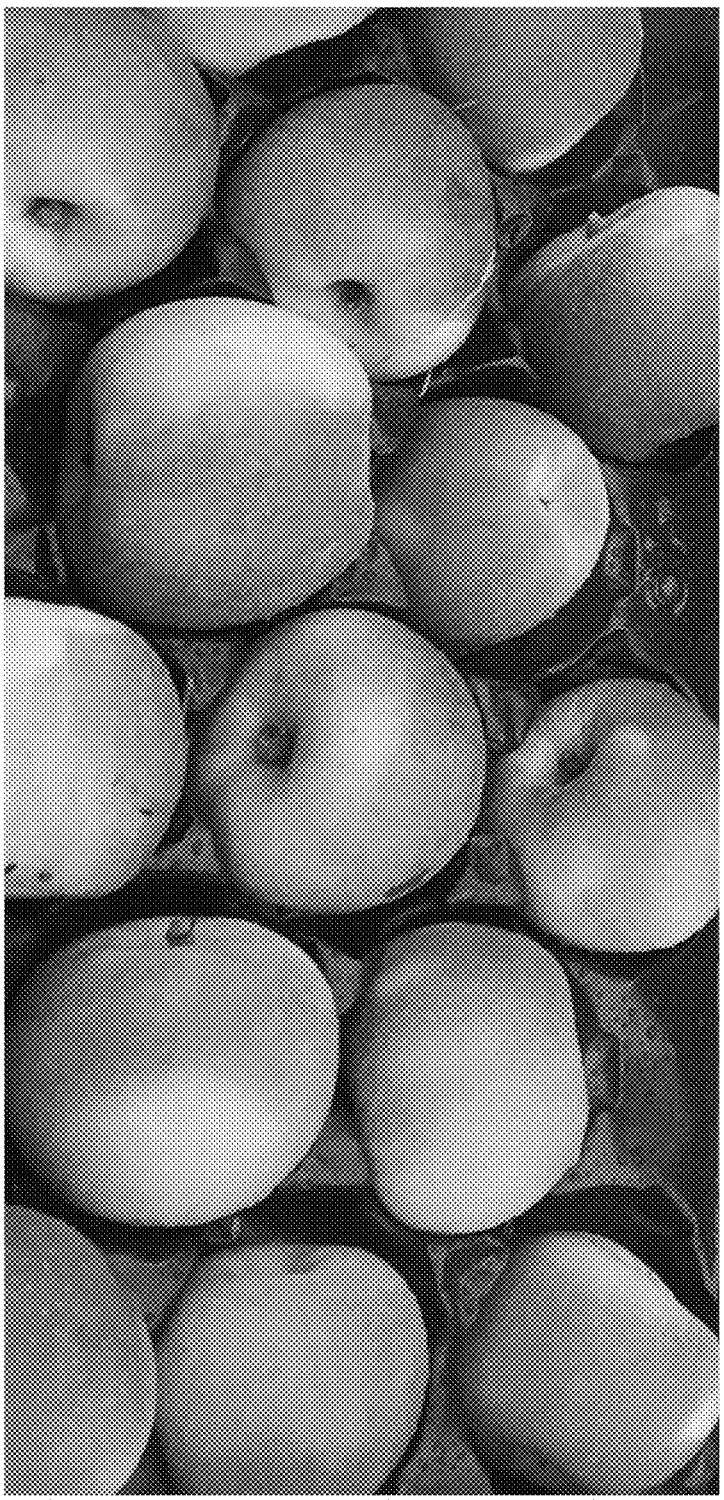
FIG. 4 is a color photograph taken on Sep. 30, 2019 of 'MD-TAP2' apple fruit harvested showing typical fruit over color, ground color, stems and calyces.
Figure 5:
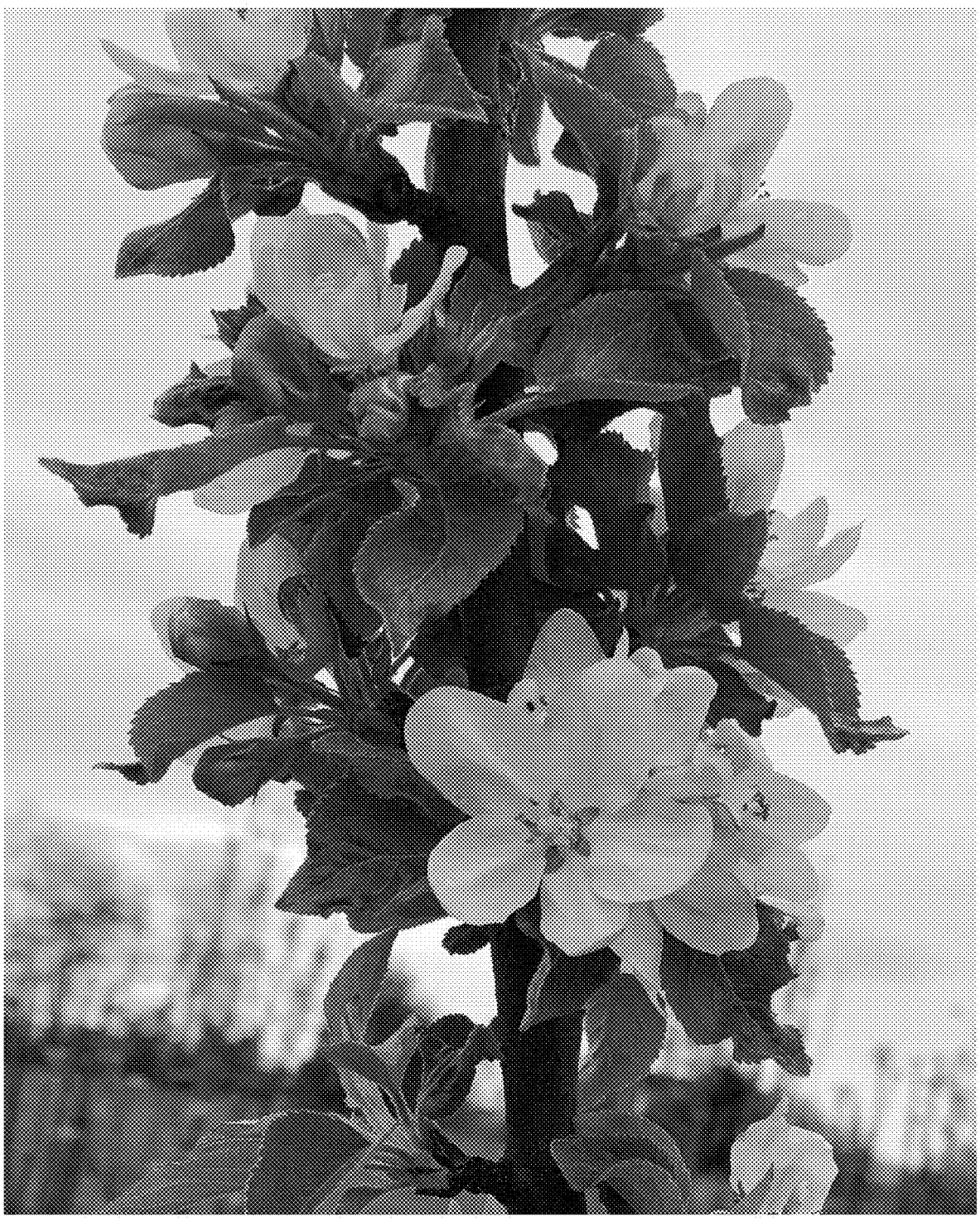
FIG. 5 is a color photograph taken on Apr. 14, 2021 of 'MD-TAP2' apple bloom showing fully opened flowers and unopened flower buds.

The following is a detailed description of 'MD-TAP2' trees that were budded onto 'M.111' rootstock and grown in Keedysville, Washington County, Md. Measurements of the fruit were taken in 2020, and the measurements of the flowers, leaves and wood were taken in 2021 and 2022. All color references are taken from The Royal Horticultural Society (R.H.S.) Colour Chart, $5^{th}$ Edition.

Scientific name: *Malus* x *domestica* Borkh.

Parentage:

*Seed parent*.—'Fuji'.

*Pollen parent*.—Seedling apple tree derived from an open pollination of 'Dwarf McIntosh' in an isolated block of 'Gala' apple trees.

Tree:

*Vigor*.—Moderate.

*Plant hardiness zone*.—Growth of plants has been observed in USDA Zone 6b.

*Dormant flower bud cold tolerance*.—At least −5° F. (−17.8° C.).

*Overall shape*.—Conical.

*Height*.—13.4 feet (4.08 cm).

*Width*.—12.5 feet (3.82 cm).

Trunk and branches:

*Trunk bark color*.—Greyed-brown (RHS 199A).

*Primary branches*.—Grey (RHS 201A).

*Branch angle*.—Ranges between 30 and 90° from the trunk.

*Lenticels*.—4.6 per cm.$^2$.

*Lenticel shape*.—Elliptical (1 mm) with the long axis parallel to the direction of shoot extension growth.

*Lenticel color*.—White (RHS NN 155D); The long axis of the ellipse is bisected by a Greyed-Orange (RHS 165C) line parallel to the direction of shoot extension growth.

*Terminal shoots*.—51 cm. in length; mid-shoot diameter 0.9 cm.

*New growth bark*.—Brown (RHS 200A).

*One-year old mid-shoot internode*.—Length: 1.3 cm; Thickness: 8.3 mm.

Leaves:

*Leaf shape*.—Ovate.

*Leaf base*.—Rounded.

*Texture*.—Upper surface smooth; lower surface slightly velvety.

*Length*.—11.8 cm.

*Width*.—5.1 cm.

*Apex*.—Acute.

*Venation*.—Pinnate.

*Margin*.—Serrated with about seven teeth per cm.

*Petioles*.—Between 2.9 and 3.5 cm. long. Color is Greyed-red (RHS 181A).

*Petiole diameter*.—2.7 mm.

*Stipules*.—Two with an average length of 8 mm.

Leaf color:

*Upper leaf surface*.—Green (RHS N137A).

*Lower leaf surface*.—Yellow-green (RHS 148B).

*Vein*.—Yellow-green (RHS 145C).

Flowers:

*Size*.—7.8 cm. diameter.

*Petals*.—5 ovate petals per flower; Petal length 2.5 cm. and width 1.8 cm.

*Petal arrangement*.—Intermediate.

*Margin*.—Smooth.

*Pistil*.—Five 8 mm long pistils are fused at their base and divide into five distinctly separate styles of 4.2 mm length at 3.8 mm above the pistils' point of attachment to the gynoecium.

*Style color*.—Yellow-Green (RHS 145A).

*Stigma shape*.—Elliptical.

*Stigma color*.—Yellow-green (RHS 145A).

*Stamens*.—Typically 18; anther color, Greyed-yellow (RHS 162B); filament Yellow-green (RHS 145D).

*Pollen*.—Brilliant yellow (RHS 11A); abundance medium.

*Flower sepals*.—Length 5 mm.; Reflexed.

*Sepal number*.—5 per flower.

*Sepal shape*.—Lanceolate with an acuminate apex and sessile base.

*Sepal margin*.—Finely dentated.

*Flower calyx shape*.—Star-shaped; Sepals meeting at the base.

*Calyx surface color*.—Green (RHS 142C).

*Pedicel length*.—16.1 mm.

*Bloom season*.—Mid-season.

*Blooming begins* (*observed in* 2022).—April 13.

*Full bloom* (*observed in* 2022).—April 28.

*Ending of bloom* (*observed in* 2022).—May 5.

Fruit:

*Size*.—Medium, averaging 7.3 cm. diameter, 6.82 cm. height, and 178 gram weight.

*Shape*.—Globose.

*Fruit eye size*.—8.5 mm. Slightly open.

*Color*.—Overcolor is Red (RHS 46A); ground color is Yellow-green (RHS 151B). Overcolor of ripe fruit ranges between 65% and 95%, averaging 80% red.

*General color effect*.—Brightly colored Red (RHS 46A) over Yellow-green background (RHS 151B) and a yellow-green (RHS 154C) stem cavity.

*Bloom*.—Slight.

*Skin*.—Smooth and waxy.

*Stem*.—Variable length, ranging from 11 mm. to 18 mm. and 3.0 mm. diameter at the mid-point.

*Fruit stalk color*.—Yellow-Green (RHS N144A) shaded side; Greyed-Orange (RHS 166A) sunny side.

*Cavity*.—Flaring and smooth. Sometimes a minimal amount of russet.

*Basin*.—Diameter ranges from 26 mm. to 37 mm. depending on fruit size. Depth averages 1.5 cm.

*Calyx*.—Calyx basin smooth; 5 sepals present.

*Calyx tube*.—Cone-shaped, Sepals persistent with closed upright tips.

*Lenticels*.—25 per cm.$^2$; Greyed-yellow (RHS 162C).

*Lenticel shape*.—Round, 0.1 mm in diameter.

*Russet*.—Minimal to none.

Fruit properties:

*Flesh color*.—Yellow (RHS 10D).

*Juice*.—Above average.

*Firmness*.—Firm; 16.0 lb. at harvest.

*Texture*.—Crisp and smooth.

*Flavor*.—Mild and aromatic.

*Soluble solids*.—11.9° Brix (mature fruit) and 14.7° Brix (tree-ripe fruit with water core).

*Aroma*.—Pleasant.

*Eating quality*.—Very good.

*Keeping quality*.—Best before 4-5 months storage.

*Harvest date*.—September 20-30 in Washington County, Md.

*Productivity of the fruit*.—Research planting yielded about 2 bushels per tree at a spacing of 330 trees per acre; at 42 lbs. per bushel, the estimated yield would be 27,720 lbs. per acre.

*Core*.—Median position; 3 cm. in diameter.

*Core lines*.—Basal; Clasping.

*Carpellary area*.—Visible.

*Depth of calyx tube*.—10 mm.

*Seed cells*.—Generally 1-2 seeds per cell. Closed; 5 in number.

*Cell walls*.—Thick and firm.

Seeds:

*Number*.—7 to 10.

*Length*.—11 mm.

*Breadth*.—5 mm.

*Form*.—Pyriform, resembling a teardrop.

*Color*.—Greyed-orange (RHS 166A).

*Plant/fruit disease and pest resistance/susceptibility*.—In addition to tree architecture which reduces pruning and training labor, 'MD-TAP2' trees have shown acceptable field tolerance to fireblight (*Erwinia amylovora*) when grown in the Washington County, Md. research orchard. Due to heavy fruit set, trees will benefit from standard crop-load management practices.

Pollination: Diploid apples with an early to mid-season bloom date. Compatibility with 'Fuji,' its seed parent, has not been tested. Due to its early bloom and parentage, some flowers may be susceptible to late spring freezes, similar to 'Delicious' (unpatented) and 'Fuji.'.

Use: For dessert.

What is claimed is:

1. A new and distinct variety of apple tree named 'MD-TAP2' as shown and described herein.

* * * * *